(12) United States Patent
Blau et al.

(10) Patent No.: US 11,666,386 B2
(45) Date of Patent: *Jun. 6, 2023

(54) SURGICAL SITE DISPLACEMENT TRACKING

(71) Applicant: Stryker European Operations Holdings LLC, Kalamazoo, MI (US)

(72) Inventors: Arno Blau, Balingen (DE); Bernd Simon, Kiel (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/172,460

(22) Filed: Feb. 10, 2021

(65) Prior Publication Data

US 2021/0186616 A1 Jun. 24, 2021

Related U.S. Application Data

(63) Continuation of application No. 16/317,649, filed as application No. PCT/US2016/042724 on Jul. 18, 2016, now Pat. No. 10,925,674.

(51) Int. Cl.
| | |
|---|---|
| *A61B 34/10* | (2016.01) |
| *G06T 7/13* | (2017.01) |
| *G06T 7/33* | (2017.01) |
| *G06T 7/00* | (2017.01) |
| *A61B 90/00* | (2016.01) |

(Continued)

(52) U.S. Cl.
CPC .............. *A61B 34/10* (2016.02); *A61B 90/37* (2016.02); *G06T 7/0014* (2013.01); *G06T 7/0016* (2013.01); *G06T 7/12* (2017.01); *G06T 7/13* (2017.01); *G06T 7/337* (2017.01); *A61B 2034/104* (2016.02); *A61B 2034/105* (2016.02); *A61B 2034/2065* (2016.02); *A61B 2090/3764* (2016.02); *G06T 2207/10116* (2013.01); *G06T 2207/30008* (2013.01); *G06T 2207/30052* (2013.01)

(58) Field of Classification Search
CPC ........... A61B 34/10; A61B 90/37; G06T 7/12; G06T 7/13; G06T 7/337; G06T 7/0014; G06T 7/0016
See application file for complete search history.

(56) References Cited

U.S. PATENT DOCUMENTS

| | | |
|---|---|---|
| 8,331,634 B2 | 12/2012 | Barth et al. |
| 8,998,909 B2 | 4/2015 | Gillman et al. |
| 10,925,674 B2 * | 2/2021 | Blau .................... G06T 7/12 |

(Continued)

OTHER PUBLICATIONS

International Search Report dated Oct. 13, 2016, for PCT/US2016/042724, 3 pages.

*Primary Examiner* — Santiago Garcia
(74) *Attorney, Agent, or Firm* — Lerner David LLP (57) ABSTRACT

A method comprises providing a current state image and at least one reference image, taken from a similar angle range. The image and the at least one reference image are superimposed and a visual representation visualizing the relation between the image and the reference image is provided in order to track displacements of the bone during subsequent operation steps. A system is provided which can use the image data to track displacements and determine deviation from a current state of the elements in question to a target state.

16 Claims, 4 Drawing Sheets

(51) Int. Cl.
    *G06T 7/12*         (2017.01)
    *A61B 34/20*     (2016.01)

(56)         References Cited

U.S. PATENT DOCUMENTS

| | | | |
|---|---|---|---|
| 2005/0203384 A1 | 9/2005 | Sati et al. | |
| 2006/0142657 A1* | 6/2006 | Quaid | A61B 17/1764 600/424 |
| 2007/0219561 A1* | 9/2007 | Lavallee | A61B 34/20 606/90 |
| 2008/0108912 A1* | 5/2008 | Node-Langlois | A61B 5/4528 600/587 |
| 2008/0119724 A1 | 5/2008 | Williamson | |
| 2009/0209884 A1* | 8/2009 | Van Vorhis | G16H 50/50 600/595 |
| 2010/0049195 A1* | 2/2010 | Park | A61B 34/10 700/98 |
| 2013/0314440 A1* | 11/2013 | Simon | G06T 7/0014 345/629 |
| 2015/0164445 A1* | 6/2015 | Blau | A61B 34/10 606/102 |
| 2015/0238271 A1* | 8/2015 | Wollowick | G06T 7/33 600/436 |
| 2015/0257846 A1* | 9/2015 | Kubiak | A61B 90/37 600/407 |
| 2015/0265361 A1* | 9/2015 | Blau | A61B 34/10 606/67 |
| 2016/0354156 A1* | 12/2016 | Blau | A61B 6/487 |
| 2018/0235715 A1* | 8/2018 | Amiot | G01B 11/25 |
| 2018/0318012 A1* | 11/2018 | Blau | G16H 20/40 |

\* cited by examiner

SURGICAL SITE DISPLACEMENT TRACKING

CROSS-REFERENCE TO RELATED APPLICATIONS

This application is a continuation, of U.S. application Ser. No. 16/317,649, filed Jan. 14, 2019, which claims priority to national phase entry under 35 U.S.C. § 371 of International Application No. PCT/US2016/042724, filed Jul. 18, 2016, published in English, all of which are incorporated herein by reference.

BACKGROUND OF THE INVENTION

The invention relates to the field of computer based assistance of surgery. In particular, the invention relates to a method and a corresponding system of automatic image processing including an interpretation of the content of for example two subsequently taken x-ray images. The method may be implemented as a computer program executable on a processing unit of a suitable device.

In every surgery where intraoperative imaging is used it is a challenging task to accurately perform the necessary steps of a procedure of treating a bone fracture. In particular displacement of a bone, a bone part or a bone fragment can easily occur in surgery steps requiring exertion of pressure or force. Such surgery step may, for instance, be a final lag screw placement, requiring exertion of greater force by a surgeon as the friction between screw and bone gets larger.

There is the risk that a displacement, such as a translation or a rotation of a bone or a bone fragment, is not detected by a surgeon.

BRIEF SUMMARY OF THE INVENTION

It may therefore be seen as an object of the invention to provide a method and device for more efficiently assisting in performing a surgical procedure.

The mentioned objects are solved by the subject-matter of each of the independent claims. Further embodiments are described in the respective dependent claims and with reference to the drawings.

According to a first aspect of the invention a method for displacement tracking during the positioning and fixing of an implant in a bone, for example a hip bone, is provided. The method comprises the step of providing an image of the bone and providing at least one reference image of the bone. The image may be the most current or latest x-ray image taken during the surgical procedure. In a further method-step the image and the at least one reference image are superimposed, wherein such superimposing requires that the image and the reference image are taken from a similar angle range. Subsequently, a relationship between the image and the at least one reference image is visualized in order to track a potential displacement of the bone or a bone fragment relative to an implant.

It would be highly beneficial to better control and point out undesired displacements of a bone or a bone fragment relative to an implant in final placement and fixing of the implant. During positioning and fixing of an implant, forces have to be exerted to achieve a good fixation of the implant in, e.g., a bone or bone portion. Force exertion may, however, lead to unwanted and undesired displacements of the bone or the implant. Such displacement may be overlooked or may not be identified by a surgeon, when the latter only considers one image of the surgical area, e.g. after final lag screw placement. The present invention provides a better control of undesired displacements by providing a visual representation of a relationship between an image and a reference image. The visualization of the relationship can help a surgeon or user to detect or better identify undesired displacements, which were caused in a surgery step after taking the reference image and before taking the current intraoperative image.

The image and/or the reference image may be an x-ray image. Further, the reference image can be provided by a database and/or can be an earlier acquired image of the bone taken from a similar angle as the image. The step of superimposing can comprise a computer internal superposition and/or a visual superposition of the image and the at least one reference image. Superimposing of the image and the at least one reference image can also comprise a matching of the scale and/or portion of the image and the at least one reference image.

The notion "similar angle range" denotes that the deviations between the angles defining the perspective from which the image is taken and the perspective from which the at least one reference image is taken are small, for instance between 0° and 5°. For such small deviations, the perspectives or viewpoints of the image and the at least one reference image are sufficiently close to each other to allow for a superimposing of the image and the at least one reference image. In this case, displacements of a bone relative to the position of an implant or relative to a background structure can be detected by comparison of the image and the at least one reference image. In particular, there is no additional need to process or adjust the image or the reference image beforehand by a rotation. A background structure in the above context—more generally in context of the invention—can be an anatomic region or part of an anatomic region depicted/visible in the image and/or the reference image, which is not displaced e.g. by a rotation or a lateral or transversal movement during positioning and fixing of an implant in a bone.

Detection of the angles from which the image and the reference image are taken, respectively, can be performed automatically—e.g. by a suitable software—by, for instance, relying on detection and identification of the position and orientation of a reference object in the image and the reference image. By determination of these angles it can be ensured that the image and the at least one reference image are indeed taken from a similar angle range, with deviations between corresponding angles in the image and the at least one reference image between, for instance, 0° and maximally 5°. Thereby, a reference object can be an object directly attached to an anatomical structure, e.g. being in contact with an outer surface of a body part of interest, or at least part of an implant, e.g. given by radiopaque spheres attached to an implant or attached to a drilling tool for fixing a bone screw. Instead or in addition to the detection of the view-point angles of the images based on a reference object visible in the respective image, also a non-rotating part of the anatomy visible in the images can be used in order to automatically—by image processing algorithms—determine the angle(s) under which the images are taken. By an automatic determination of the angles, from which the images are taken, and, consequently, an automatic determination of the deviation between corresponding angles related to the image and the at least one reference image it can be ensured automatically, that the angle range of the at least two images is similar. As a consequence, if the deviation between corresponding angles in the image and the at least one reference image would exceed e.g. a deviation of 5° a warning could be generated and further method steps would not be performed unless a new/another image with a similar angle range as the reference image would be available. In this way it is automatically ensured that the deviation between the angles under which the image and the at least one reference image are taken is small enough.

As an example, displacement of the bone or a bone fragment can occur in final lag screw placement—that is during the last few turns of a lag screw before the screw is brought in its final position. In this case, the friction between the screw and the bone can get so high that, for instance, proximal fragments could rotate and thereby be displaced from their desired position. The risk for such displacement is higher the more unstable a fracture.

According to an embodiment of the invention, the visualization of the relationship between the image and the at least one reference image comprises visually representing the image and the least one reference image in juxtaposition.

Visualization can be performed by an imaging unit, the imaging unit comprising a display for visual representation. The imaging unit can be part of an imaging system comprised in a medical device. The imaging unit can, however, also be a separate imaging unit to which the image and the at least one reference image are provided.

According to an embodiment of the invention, the most current image and the at least one reference image may be visually represented on a display in juxtaposition, for instance side by side or one above the other.

According to an embodiment of the invention, the visualization of the relationship between the image and the at least one reference image comprises a switching between a visual representation of the image and a visual representation of the at least one reference image.

This implies that the image and the at least one reference image are visualized, e.g. displayed on a computer display, one at a time and that a surgeon or user can switch or toggle between the two visualizations. Such switching or toggling can also be done automatically, e.g. by subsequently showing the image and the at least one reference image for a predetermined time period, respectively.

According to an embodiment of the invention, the step of visualizing comprises a combined visual representation of the current image and the at least reference image. In other words, the image and the at least one reference image are simultaneously visualized in superposition.

In this case it is preferred that the image and the at least one reference image have a color marking of objects or devices in the respective image. In addition to or instead of a color marking, the image and the at least one reference image can have a marking by hatching or shading. The color marking and/or hatching and/or shading can be the same or can be different in the image and the at least one reference image. As an example, the lag screw in the image may be colored differently from the lag screw in the at least one reference image. In this case, the different colors can help to indicate to a surgeon a possible displacement of lag screw in the image with respect to the at least one reference image.

According to an embodiment of the invention, the step of visualizing is done for a series of images of the bone, the series of images comprising the image and a set of reference images.

Depending on the workflow, more than one reference image may be available in a database or might have been taken in a previous surgery step. In this case the before and hereinafter described visualization may comprise a visualization of the current image and all available reference images, or a selectable or predetermined subset of the reference images. Selection of the reference images to be visualized can be done by hand or according to a timeline. For instance, only a set of the latest taken reference images or reference images taken in a predetermined time period can be selected automatically.

According to an embodiment of the invention, the most current image and the at least one reference image comprise at least one reference body. The superimposing of the image and the at least one reference image can then be based on the reference body in the image and the at least one reference image.

A reference body can be one of a bone, a bone portion, a bone shape, an implant or an additional reference object.

An additional reference object may be directly attached to an anatomical structure, e.g. may be in contact with an outer surface of a body part of interest. The reference object may also be indirectly coupled to an anatomical structure, for example via a handling tool for inserting an implant. On the other hand, the reference object may be at least a part of an implant. In other words, an implant which is adapted to be fixed at or in a bone may comprise elements which can be identified in an image of the bone or at least a section of the bone so that geometrical aspects may be determined based on the identified elements. For example, the elements may define points so that two elements may define a line or an axis, or the elements may define a contour so that a center axis may be determined.

According to an embodiment of the invention, the method further comprises the step of detecting an outline of the bone in the image and in the at least one reference image. The method-step of superimposing can then be based or rely on the detected outline in the images. In other words, the outline can be used in the process of superimposing and matching of the most current image and the at least one reference image.

For outline detection, grayscale values of pixels may, for instance, be identified and compared with adjacent pixel grayscale values so as to detect contour lines or points in the image and the at least one reference image, respectively. The contour lines can than used to determine or define an outline of an object, e.g. a bone or an implant, in the image and the at least one reference image.

According to an embodiment of the invention, the method-step of superimposing the image and the at least one reference image is based on a pixel wise comparison of the pixels in the image and the reference image. Alternatively, an area wise comparison or a comparison of clusters of pixels in the image and the reference image can be performed.

Hence, the step of superimposing can generally rely on a difference analysis of the images.

According to an embodiment of the invention, the step of superimposing the current image and the at least one reference image comprises only an adjusting of a section and/or a scale of the image and the at least one reference image. In addition, or alternatively, adjusting of a portion of the image and/or the at least one reference image may be comprised in the step of superimposing the image and the at least one reference image.

The image and the reference image can be taken from the same angle, but from differing distances. In the latter case, the scale of the image and the reference image has to be adjusted before a visual representation of both images for further visual comparison by a user is provided. This might comprise choosing of a portion of the image or a portion of the at least one reference image to be superimposed, as either the image or the at least one reference image might show a larger region. In another case the section or detail of the image and the reference image may differ, while they are taken from the same angle and from the same distance. Then the common overlap or intersection of both images should be determined in the step of superimposing and the further image processing—comprising the visualization—refers to the respective detail of the image and the reference image which is comprised in both the image and the reference image. Determination of the common overlap or intersection of both images may in particular be based on determination of the position and orientation of a reference body or parts of a reference body visible in both images.

According to an embodiment of the invention, the angle range between the image and the at least one reference image is between 0° and 5°, preferably 0° and 4°, more preferably 0° and 3°. For this angle range, the perspectives or viewpoints of the image and the at least one reference image are sufficiently close to allow for a superimposing. In other words, for an angle range between 0° and 5°, the current image and the at least one reference image have a common viewing angle of a surgery area or region of interest. Given the common viewing angle, displacements of a bone relative to the position of an implant or relative to a background structure, such as surrounding tissue, can be detected by comparison of the image and the at least one reference image without the beforehand need to process or adjust the image or the reference image by a rotation. A comparison of the image and the at least one reference image relies on superimposing the image and the at least one reference image.

A surgery area or region of interest in this context may be a bone and the bone-surrounding area of a patient.

According to an embodiment of the invention, in a further method-step a distinction between primary structures and non-primary structures in the image and the reference image is performed. Non-primary structures are subsequently removed and only the primary structures are depicted or shown in the visual relationship of the image and the reference image. Thereby, a primary structure can be at least one of a bone, a bone shape, a bone fragment, an implant, a reference body and/or an additional reference object. An example for a non-primary structure might be surrounding tissue structure which might not be of particular relevance in lag screw placement.

In addition to or instead of any of the aforementioned or below described method steps it can be advantageous to detect or determine in a method step those objects in the image and the at least one reference image, which could potentially be displaced during positioning and fixing of an implant in a bone, and whose displacement is undesired. For instance, displacement of a bone or part of a bone during final lag screw placement is undesired and a corresponding displacement should be visualized in order to provide an indication and/or corresponding warning to a surgeon. However, also e.g. the tip of a lag screw will be displaced during final lag screw placement. The corresponding displacement of the lag screw can be desired and displacement of only the lag screw may not be particularly marked and/or colored in a visualization in the image and the at least one reference image. Generally, displacements of anatomical parts in the images may be visualized, e.g. by different color marking or in any other of the above and below described ways, but a desired displacement of the lag screw will not be particularly marked. A desired displacement of a lag screw may be a displacement where the tip of the lag screw is moved forward in direction of the longitudinal axis of the screw. An undesired displacement of a lag screw, however, might be a displacement where the tip of the screw is bent away from the direction given by the longitudinal axis of the screw, and such lag screw displacement might be visualized. In order to automatically detect those object in the image and the at least one reference image whose displacement shall be indicated to a surgeon by means of the method described herein, a database with such objects—comprising the form and shape of these objects—can be provided and image recognition techniques can be used in order to identify those objects in the images. A corresponding database comprising such objects can, for example, comprise information of the form and shape of a femur, part of a femur, or the head of a femur.

According to an embodiment of the invention, the at least one reference image is an earlier acquired image of the bone.

According to an embodiment of the invention, the image is acquired after detection of a relevant surgery step. A relevant surgery step in the context of the invention can be a surgery step suitable for displacing the bone, a part of the bone or an implant.

For instance, during final lag screw placement, displacement of the bone, a bone part or an implant can occur during the last few turns of a lag screw needed to bring the screw in its final position. Typically, the force to be applied for the last few turns of a lag screw gets high, such that unwanted and undesired displacements can easily occur. The final lag screw placement step can be detected by image processing methods detecting various objects or devices and their relative position in an image. In this way the progress and point in the workflow of a surgery can be determined, including, for instance, the step of final lag screw placement. For example, the image processor can determine when a head portion of a lag screw contacts bone or an implant on the bone by analyzing the image and reference images. Alternatively, or in addition, the image processor can determine when a tip portion of a lag screw starts to enter or enters into robust bone material by analyzing the image and the reference image. For instance, robust bone material can be identified by analyzing the texture of respective portions of the bone in the image and the reference image. If a lag screw starts to penetrate into robust bone material, the friction between screw and bone increases in this region and the risk of a rotation of e.g. a bone fragment in this region rises when a force is exerted in order to turn the screw. Such situation may happen in the last turns of a lag screw, when the tip portion of the screw may enter into a robust bone material where it is fixated.

As used herein, the term "anatomical structure" refers to anything at a bone and in particular to a geometrical aspect of a bone, i.e. a point, a line, an arc, a centre point, an axis, a cylinder surface, a ball surface, or the like. For example, a geometrical aspect of a femur may be the outer surface of the femur head, an axis defined by the neck between shaft and femur head, a longitudinal axis of the femur shaft, a most distal point on the bone surface, a line defined by the centre points of the condyles, or a line defined by the most posterior points at the condyles. It will be understood that the other bones provide other and/or comparable suitable geometrical aspects.

A computer program element capable of performing steps of the method may comprise sets of instructions for identifying a current state of each of the detected elements. Here, "current state" means first of all a position and orientation of the detected element. As will be described in detail below, the position and orientation of the reference body can be determined due to the specific distribution of fiducial markers forming the reference body. With respect to an instrument, like a gauge or a drill or a K-wire, the position may be detected in relation to the reference body and/or to an anatomical structure. A "current state" of an instrument may also include a deformation or bending of the instrument. Furthermore, a "current state" may indicate the appearance of the instrument and/or of an implant or sub-implant in the 2D projection image.

Based on the identified state of the detected elements, a state of progress of the procedure of fracture treatment may be determined. For example, a processing unit may execute sets of instructions so as to compare information provided by a database with the results of the previously performed steps, with the database including data defining each step out of a sequence of steps necessary to perform a fracture treatment procedure. For example, the steps may be defined in the database by the respective state of the elements which elements are involved in the particular step, so that information extracted from the 2-D projection image can be compared with information received from the database.

The step following the identified step out of the sequence of steps in the database may be used by the processing unit to provide information which step should be performed next. Such information can, for example, be shown on a monitor as information assisting in the fracture treatment.

When comparing the database information with the identified state of the detected elements, a processing unit, when executing sets of instructions of the computer program element, may determine a deviation of the current state of the element from a target state of the element in which the element should be in the determined state of progress. Further, a degree of deviation may be determined, and the degree of deviation may be compared with a predetermined threshold value. In a case in which the determined deviation exceeds the threshold value, at least a warning may be provided, but also a suggestion to undo a step.

The determined deviation may also be translated by a processing unit into an adjustment movement of an extracorporeal handling device, i.e. a handling device being outside of a body of a patient. For example, an adjustment movement may be a translational or a rotational movement of a handle of an instrument in a specific direction so as to shift an implant in a longitudinal direction thereof or to tilt or rotate the implant. The kind and degree of the adjustment movement may be optically or acoustically provided.

A system for displacement tracking during positioning and fixing of an implant in a bone, in particular a hip bone, is provided according to a second aspect of the invention. The system comprises an imaging unit and a processing unit. The imaging unit is configured to provide an image of the bone and to provide at least one reference image. Thereby, the at least one reference image can be an earlier acquired imaged stored in a storage unit of the imaging unit, or the reference image can be provided from a database of the imaging unit. The at least one reference image can also be provided from an external storage device and can, in this case, be acquired by a different imaging unit or different system at a previous point in time. The processing unit is configured to superimpose the current state image with the at least one reference image. To this end, the image and the at least one reference image are taken from a similar angle range. The processing unit is further configured to visualize the relationship between the image and the reference image in order to allow for tracking of displacement of the bone relative to the implant.

An imaging unit may be an imaging device of a medical device, for example an X-ray imaging system. The imaging unit may be configured to acquire images of a surgical area. The imaging unit may comprise a display or a monitor for visualizing images, information, and/or text.

A processing unit may be a processing unit of a computer. The computer may be comprised in a medical device or may be connectable to a medical device. The processing unit can comprise a processor, which can be configured to process data or to work on data delivered to the processor.

According to an embodiment of the invention, the image and reference image are intraoperative images taken at different times. Thereby, the image and/or the reference image may be taken by the imaging unit of an above described system.

According to a third aspect of the invention, a computer program is provided, which, when executed by a processor, can perform the method-steps described above.

According to a fourth aspect of the invention, a computer readable medium is provided, on which the above described computer program is stored.

It has to be noted that embodiments are described with reference to different subject-matters. In particular, some embodiments are described with reference to method type claims whereas other embodiments are described with reference to apparatus type claims. However, a person skilled in the art will gather from the above and the following description that unless other notified in addition to any combination of features belonging to one type of subject-matter also any combination between features relating to different subject-matter is considered to be disclosed with this application.

BRIEF DESCRIPTION OF THE DRAWINGS

The aspects defined above and further aspects, features and advantages of the present invention can also be derived from the examples of the embodiments to be described hereinafter and are explained with reference to examples and embodiments also shown in the figures, but to which the invention is not limited.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

Figure 1:
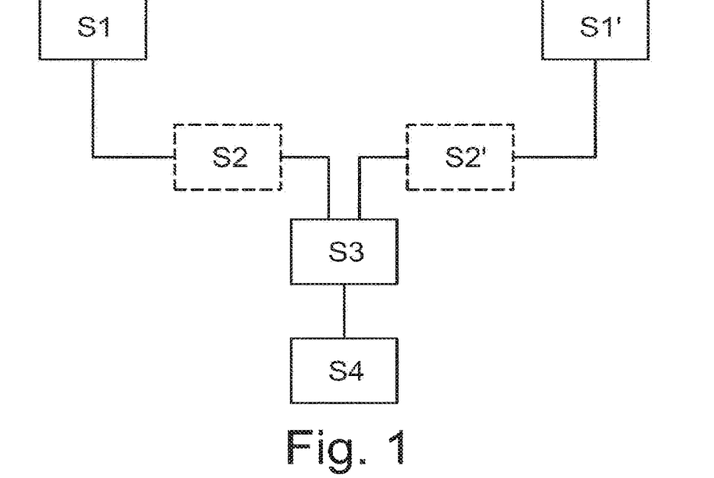
FIG. 1 shows a flow chart of steps of a method according to an embodiment of the invention.

The flow-chart in FIG. 1 illustrates method steps performed in accordance with embodiments of the invention. It will be understood that the steps described may be major steps, wherein these major steps might be differentiated or divided into several sub-steps. Furthermore, there might be also sub-steps between the steps. Consequently, groups of steps may be related to a major aspect which may also be performed separately, i.e. independent from other steps or groups of steps.

It is noted that some steps are described as being performed "if necessary". This is intended to indicate that those steps may be omitted. It is in particular noted that a computer program element according to an embodiment of the invention may comprise sets of instructions to automatically recognize if a step is necessary or not, and to automatically proceed with the next actually necessary step.

With reference to FIG. 1, the exemplary method starts with providing an image of a bone in step S1. The image may be an x-ray image. Alternatively, the image may be an ultrasound image, a magnetic resonance image or any another type of image acquired in medical diagnostics and/or therapy. In method step S1' a reference image of the bone is provided. The reference image may or may not be or the same type of image as the image of the bone provided in step S1.

It is intended that the image and the reference image are taken from a similar angle range. For instance, the deviation between the points of view/angles under which the image and the reference image are taken can be between 0° to 5°, but should not be significantly larger.

It should be noted that the time-wise order of provision of the image and the reference image, that is the order of steps S1 and S1', is arbitrary. The image can be provided first and the reference image can be provided subsequently, or vice versa. If necessary, the image and the reference image are processed/analyzed, respectively, in subsequent optional steps S2 and S2'. It should further be noted that the image is typically the last image taken/acquired of the site and that the reference image may be an earlier acquired image. That is, as far as acquisition of the image is concerned, the image is the last image taken. However, the order in which the image and the reference image are provided within the method is arbitrary.

In steps S2 and S2', an outline of the bone or of another object in the image and in the reference image can be detected, respectively. Detection of an outline in an image may rely on identification of grayscale values of pixels, which are compared with adjacent pixel grayscale values in the respective image so as to detect contour lines or points in the image.

In method step S3, the image and the reference image are superimposed. Superimposing the image and the reference image can, for instance be based on a pixel-wise comparison of, for instance, the gray scale values of the image and the reference image. Alternatively, a comparison of predetermined or adjustable areas in the image and the reference image or a comparison of clusters of pixels can be performed as a sub-step of method step S3.

As a further sub-step to method step 3, optionally, the section and/or scale of the image and the reference image is adjusted. Such sub-step can be necessary if the detail in the reference image differs from the detail in the image. In this case the image and/or the reference image can be cut to size such that the potentially "trimmed" images show the same detail. In addition, or instead of, it might be necessary to adjust a section and/or a scale of the reference image and the image, which can also be performed as part of a sub-step of the superimposing method step S3.

In next method step S4 a relationship between the image of the bone and the reference image is visualized, for instance on a computer display or a computer screen/monitor. In displaying the relationship between the image and the reference image, differences can optionally be highlighted.

Figure 2:
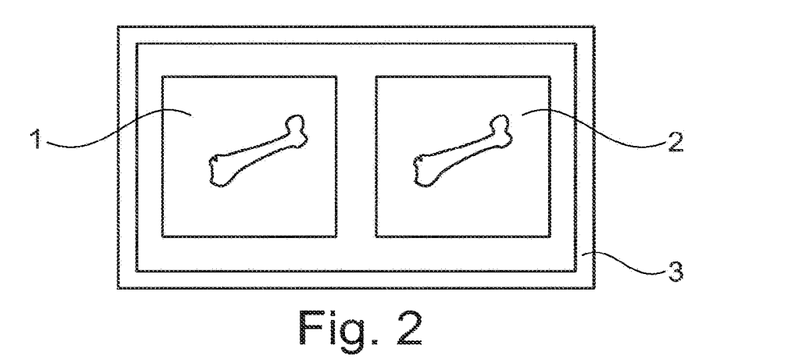
FIG. 2 shows a schematic illustration of a monitor visualization of the image and the at least one reference image according to an embodiment of the invention.

With reference to FIG. 2, a display 3 for visualizing the image of the bone as well as the reference image in order to show a relationship between these images is shown. The image 1 and the reference image 2 are shown in juxtaposition, in particular next to each other. A surgeon or user can then identify by eye differences between the image and the reference image. An illustrative example of an image and a reference image will be further discussed below in context of FIGS. 4A and 4B.

Figure 3:
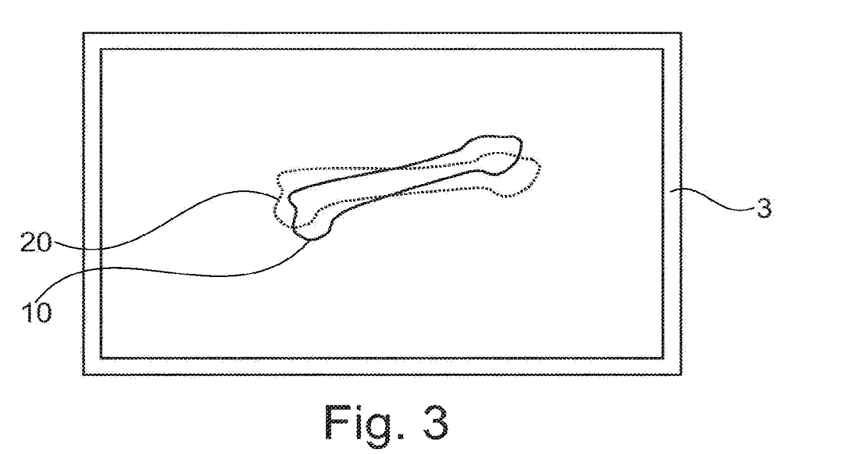
FIG. 3 is another schematic illustration of a monitor visualization of the image and the at least one reference image according to an embodiment of the invention.

In FIG. 3, another example for a display 3, which can be used for visualizing the relationship between an image and at least one reference image is shown. On the display 3 a combined visual representation of an image and a reference image is shown: both images comprise a femur and in the combined visual representation of the two images the image of the femur 10 comprised in the image is shown with solid outline. The image of the femur 20 comprised in the reference image is shown with dashed outline. In another embodiment not shown in FIG. 3, the image of the femur 10 comprised in the image and the image of the femur 20 comprised on the reference image can be visualized together—that is at a time—on display 3 with a specific color marking. For instance, the image of the femur 10 can be visualized in a color differing from the color used for displaying the image of the femur 20. Alternatively, or in addition, a different shading and/or a different hatching can be used in order to visualize the image of the femur 10 and the image of the femur 20 together on display 3. The combined visual representation of femur 10 and femur 20 can provide support for a surgeon or user in order to detect or track displacements of the femur. Such displacement can, for instance, arise during final lag screw placement, when the force exerted by a surgeon in order to finally fix the screw in the bone material is typically largest during implant-fixing-workflow.

Figure 4A:
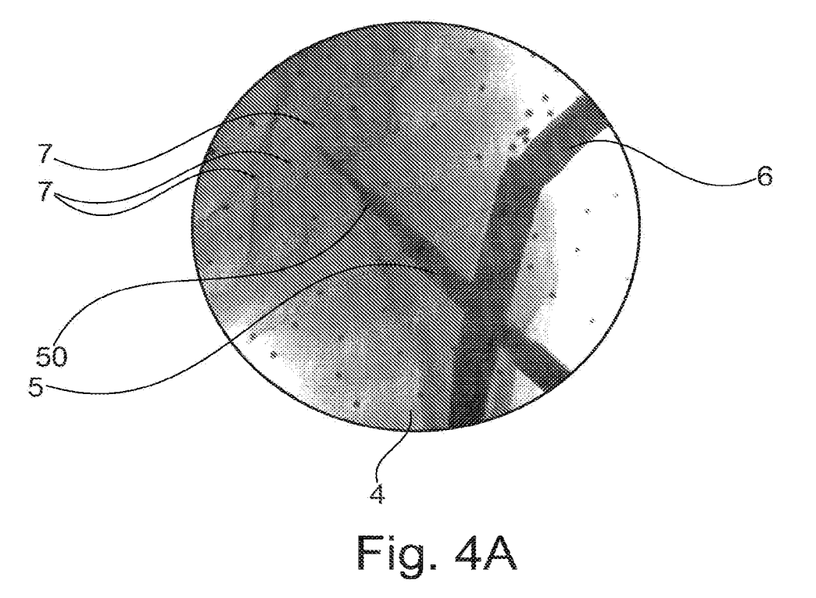
FIGS. 4A and 4B show examples of a monitor visualization of an image and a reference image according to an embodiment of the invention.
Figure 4B:
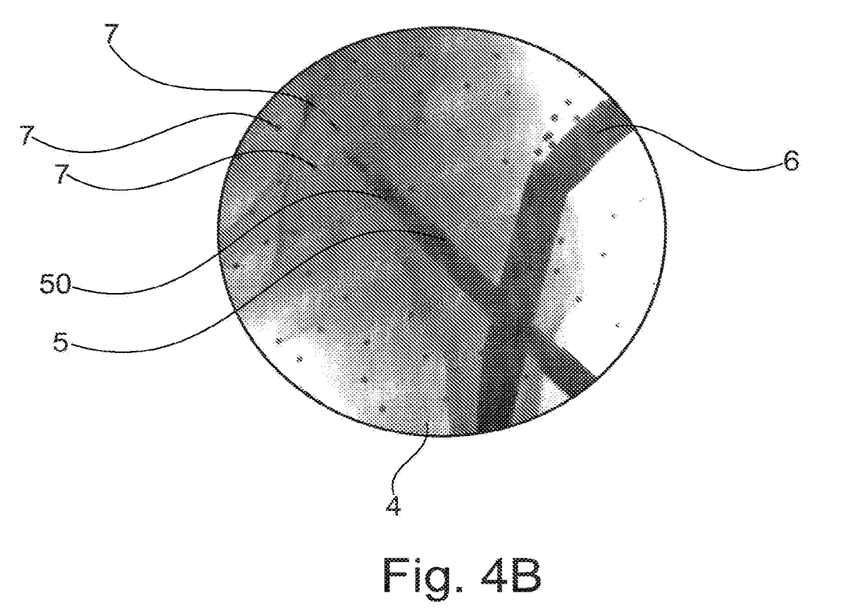

With reference to FIGS. 4A and 4B, an example of a reference image and a corresponding image are shown. FIG. 4A shows a reference image with a hip bone 4 and an implant, given by a lag screw 5. Further shown are a reference body, which may be a connector 6 to a targeting instrument and a plurality of additional reference objects. The additional reference objects shown in FIG. 4A are markers 7, which can be of use in the determination of a spatial arrangement and orientation of the further objects shown in the images relative to each other. To this end, the position of objects relative to a marker or a set of markers can be determined and from this a spatial arrangement of the objects relative to each other can be deduced. This can, for example, lead to the determination of the position of the tip of lag screw 5 within the bone 4. In FIG. 4B the same surgery area is shown, containing the same object as the reference image of FIG. 4A. However, the position of the tip portion 50 of lag screw 5 differs in the image from its corresponding position in the reference image. The image has been acquired after a few more turns of the screw into the bone material have been performed. This requires exertion of a force, and the visual representation of the image and the reference image according to embodiments of the invention can support a surgeon to identify displacements of the implant or the bone, which occurred during operation steps performed in the time during taking of the reference image and the image.

Figure 5:
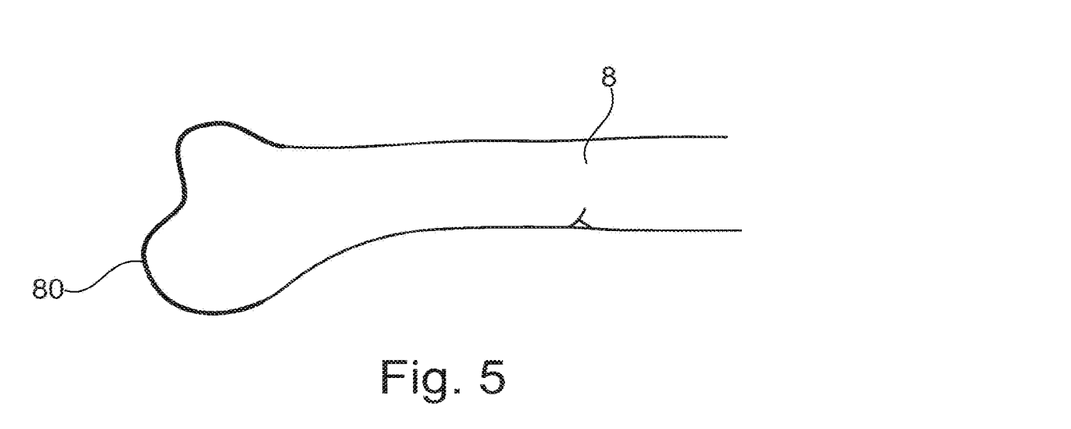
FIG. 5 shows an example of an outline of a bone according to an embodiment of the invention.

In FIG. 5, an example of an outline 80 of a hip bone 8 is shown. For instance, by identification of grayscale values of pixels in the image and the reference image and comparison with adjacent pixel-greyscale values, contour lines of a bone, e.g. a hip bone, can be detected in the image and the reference image, respectively. From these contour lines an outline of the bone can be derived, wherein the outline refers to the silhouette of the bone visible before the background in the image or the reference image, respectively.

Figure 6:
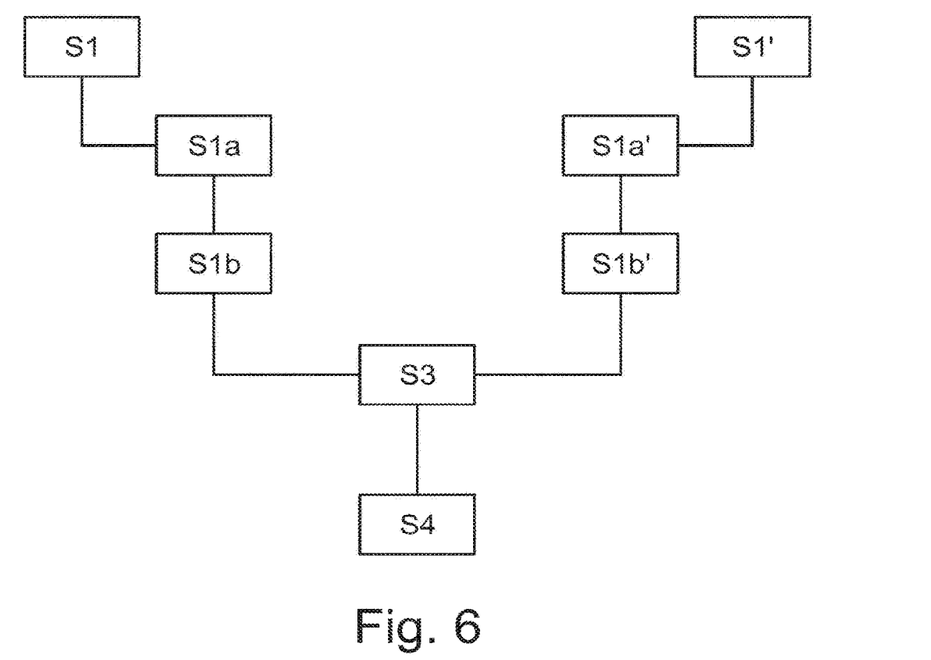
FIG. 6 shows another flow chart of steps of a method according to an embodiment of the invention.

FIG. 6 illustrates steps performed in accordance with embodiments of the method according to the invention. Similar to the first steps described with reference to FIG. 1, the method illustrated in FIG. 6 starts with provision of an image in step S1 and provision of at least one reference image in step S1'. The order of provision of the image and the reference image, that is the time-wise order of steps S1 and S1' is arbitrary. In a next steps S1a, the image is analyzed and primary structures depicted in the image are distinguished from non-primary structures. A primary structure in this context is a structure of interest for the surgical procedure. For instance, during final lag screw placement in a hip bone, primary structures can be at least one of the hip bone, the implant and the lag screw. A non-primary structure can be the tissue surrounding the surgical area. It can be intended that a user or surgeon can identify which structures are to be treated as primary structures and which structures should be considered as non-primary structures. To this end, an input unit can be provided, which is configured to send or deliver the corresponding information to a processing unit, which is configured to perform the distinction between primary and non-primary structures. Similar to the case of the image, the reference image can be analyzed and primary and non-primary structures can be distinguished therein in method step S1a'. Steps S1a and S1a' can be performed in parallel or one after the other.

In step S1b, structures that have been identified as non-primary structures in the image are removed from the image and only the primary structures are kept in the image for later visual representation. A similar procedure is performed in method step S1b' for the case of the reference image. After method steps S1b and S1b' have been performed, the resulting image and reference image are superimposed in step S3, and a visual representation of the image and the reference image, which is used in order to track displacements of, e.g. a bone shown in both images, is given in step S4.

It is understood, that the image and the reference image are taken from a similar angle range. Further, it is understood by the person skilled in the art, that the method steps explained with reference to FIG. 6 can be combined with method steps described in connection with FIG. 1.

Figure 7:
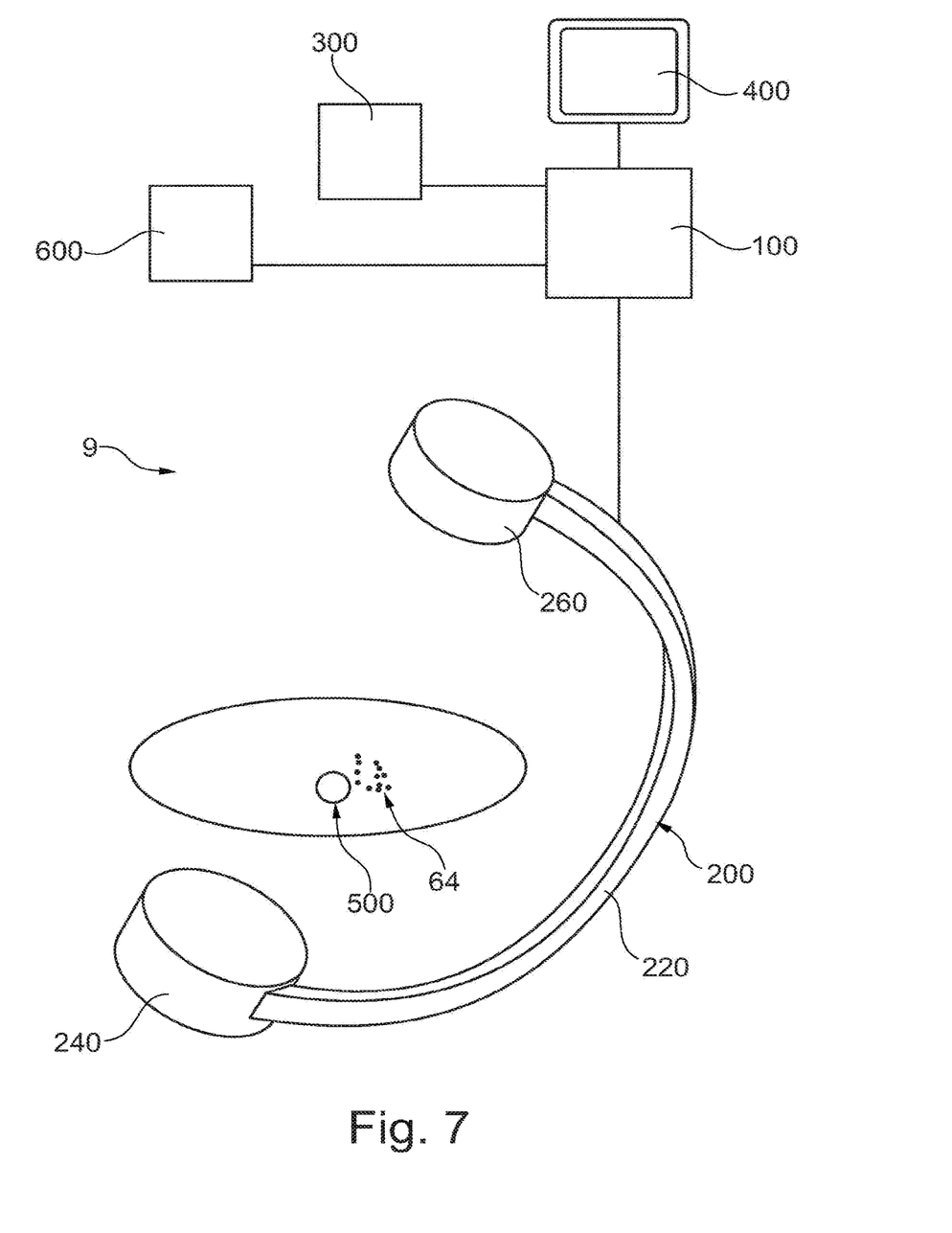
FIG. 7 shows a schematical illustration of a system according to an embodiment of the invention.

FIG. 7 shows an exemplary embodiment of a system 9 according to an embodiment of the invention. Substantially, necessary for performing the steps of the method, a processing unit 100 is part of the device.

An exemplary imaging device or imaging unit 200 includes an X-ray source, and an X-ray detector 260, wherein these two units are mounted on a C-arm 220.

Furthermore, the system 9 in FIG. 7 includes an input unit 300, by means of which for example an intended imaging direction may be manually entered. Further, a user can input structures, which shall be considered as primary structures in the images. Also shown is a connection to a database 600, located for example in a network. The database 600 may comprise information regarding anatomical structures, for example from 3D scans of different anatomical structures, so that the imaged anatomical structure may be compared with this information so as to determine or identify specific anatomical structures. The database may further comprise information regarding a sequence of necessary and/or possible steps of a surgical procedure. Further, the database can comprise a storage comprising at least one or a series of earlier acquired reference images. It is noted that it is also possible to automatically determine the progress of the surgical procedure based on detectable aspects in an x-ray image, wherein such aspects may be in instrument and/or implant. For instance, the distance of a tip portion of a lag screw from robust bone material or from an outline of a bone may be automatically determined by analysing the image and the reference image. In such a way it can be determined or estimated how many turns of a lag screw may still be necessary to bring, e.g. the tip portion of the screw in contact with robust bone material. Alternatively, the tip portion may already be in contact with robust bone material and may be close to its final position, which refers to a certain distance between the tip of the screw from an outline of a bone. From a determination of the distances between the tip portion of the screw and e.g. an outline of the bone the number of screw turns needed to fixate a predetermined portion of the tip in the bone material without arriving at the outline may be determined.

Finally, there is an indication in FIG. 7 of an anatomical structure of interest 500 as well as of a reference object 64 formed by a plurality of radiopaque spheres. Within said anatomical structure, for example a bone of a patient may be located which may be subject to the described procedures.

While embodiments have been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures can not be used to advantage. The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for displacement tracking during positioning and fixing of an implant in a bone, in particular in a hip bone, the method comprising:

superimposing an image of the bone with at least one reference image, wherein the image of the bone is taken from a first angle and the at least one reference image is taken from a second angle, wherein the difference between the first angle and the second angle is no more than 5°;
visualizing a relationship between the image of the bone and the at least one reference image for tracking a displacement of the bone relative to an implant;
distinguishing between primary structures and non-primary structures in the image of the bone and in the at least one reference image; and
removing the non-primary structures and depicting only the primary structures in the image of the bone and in the at least one reference image;
wherein each of the primary structures is at least one of a bone, a bone shape, a bone fragment, an implant, a reference body and/or an additional reference object.

2. The method according to claim 1, further comprising:
detecting or determining objects in the image of the bone and the at least one reference image, which could potentially be displaced during positioning and fixing of the implant in the bone,
wherein a displacement of a lag screw is not marked in the image of the bone or in the at least one reference image.

3. The method according to claim 1, further comprising:
analyzing a texture of the bone in the image of the bone and the at least one reference image by an image processor.

4. The method according to claim 1,
wherein the step of visualizing comprises juxtaposing a visual representation of the image of the bone with a visual representation of the at least one reference image.

5. The method according to claim 1,
wherein the step of visualizing comprises switching between a visual representation of the image of the bone and a visual representation of the at least one reference image.

6. The method according to claim 1,
wherein the step of visualizing comprises combining a visual representation of the image of the bone and a visual representation of the at least one reference image,
wherein the image of the bone and the at least one reference image have different color markings.

7. The method according to claim 1,
wherein the image of the bone and the at least one reference image each include at least one reference body, and
wherein the step of superimposing the image of the bone and the at least one reference image is based on the at least one reference body in the image of the bone and in the at least one reference image.

8. The method according to claim 7,
wherein the at least one reference body is one of a bone, a bone portion, a bone shape, an implant or an additional reference object.

9. The method according to claim 1, further comprising a step of:
detecting an outline of the bone in the image of the bone and detecting an outline of the bone in the at least one reference image,
wherein the step of superimposing the image of the bone and the at least one reference image is based on the detected outlines in the image of the bone and in the at least one reference image.

10. The method according to claim 1,
wherein the step of superimposing the image of the bone and the at least one reference image is based on a pixel wise comparison, an area wise comparison or a comparison of clusters of pixels in the image of the bone and in the at least one reference image.

11. The method according to claim 1,
wherein the step of superimposing comprises only adjusting a section and/or a scale of the at least one reference image and the image of the bone.

12. The method according to claim 1,
wherein the at least one reference image is an earlier acquired image of the bone.

13. The method according to claim 1,
wherein the image of the bone is acquired after detection of a surgery step suitable for displacing the bone, a part of the bone or an implant.

14. A system for displacement tracking during positioning and fixing of an implant in a bone, in particular in a hip bone, comprising:
an imaging unit, and
a processing unit,
wherein the imaging unit is configured for providing an image of the bone and at least one reference image,
wherein the processing unit is configured for:
superimposing the image of the bone with the at least one reference image, wherein the image of the bone is taken from a first angle and the at least one reference image is taken from a second angle, wherein the difference between the first angle and the second angle is no more than 5°,
visualizing a relationship between the image of the bone and the at least one reference image for tracking a displacement of the bone relative to an implant,
distinguishing between primary structures and non-primary structures in the image of the bone and in the at least one reference image, and
removing the non-primary structures and depicting only the primary structures in the image of the bone and in the at least one reference image,
wherein each of the primary structures is at least one of a bone, a bone shape, a bone fragment, an implant, a reference body and/or an additional reference object.

15. The system of claim 14 wherein the image of the bone and the at least one reference image are intraoperative images taken at different times.

16. A non-transitory computer readable medium containing instructions, which, when executed by one or more processors, cause the one or more processors to perform a method, the method comprising:
superimposing an image of the bone with at least one reference image, wherein the image of the bone is taken from a first angle and the at least one reference image is taken from a second angle, wherein the difference between the first angle and the second angle is no more than 5°, and
visualizing a relationship between the image of the bone and the at least one reference image for tracking a displacement of the bone relative to an implant;
distinguishing between primary structures and non-primary structures in the image of the bone and in the at least one reference image; and
removing the non-primary structures and depicting only the primary structures in the image of the bone and in the at least one reference image;

wherein each of the primary structures is at least one of a bone, a bone shape, a bone fragment, an implant, a reference body and/or an additional reference object.

* * * * *